United States Patent [19]

Nuwayser

[11] Patent Number: 4,834,978
[45] Date of Patent: May 30, 1989

[54] METHOD OF TRANSDERMAL DRUG DELIVERY

[75] Inventor: Elie S. Nuwayser, Wellesley, Mass.

[73] Assignee: BIOTEK, Inc., Woburn, Mass.

[21] Appl. No.: 153,147

[22] Filed: Feb. 8, 1988

Related U.S. Application Data

[63] Continuation of Ser. No. 920,300, Oct. 17, 1986, abandoned, which is a continuation-in-part of Ser. No. 653,362, Oct. 1, 1984, Pat. No. 4,624,665.

[51] Int. Cl.$^4$ ............................................. A61F 13/02
[52] U.S. Cl. ................................. 424/448; 424/423; 424/449
[58] Field of Search ............................... 424/449, 448

[56] References Cited

U.S. PATENT DOCUMENTS 4,624,665 11/1986 Nuwayser ........................... 604/307

Primary Examiner—Thurman K. Page
Assistant Examiner—P. L. Prater
Attorney, Agent, or Firm—Richard P. Crowley

[57] ABSTRACT

A transdermal drug delivery system useful for the controlled, for example, zero order, release of one or more drugs to a selected skin area of a user, which system comprises a reservoir containing a transdermal delivery composition. The reservoir contains a composition which comprises a base material, which is a solid but which melts or liquefies upon contact with the skin of a user and selected to occlude the skin of the user to force hydration of the stratum corneum with water from the lower layers of the epidermis of the user and a plurality of solid microparticles, generally uniformly dispersed and suspended in the base material, the microparticles containing an effective, therapeutic amount of the drug for transdermal delivery, such as the contraceptive steroid. In use, the base material forms a thermodynamically stable thin film layer in intimate contact with the skin while the drug is released from the microparticles into the base material and transdermally into the user through the thin liquid film of the base material.

23 Claims, 2 Drawing Sheets

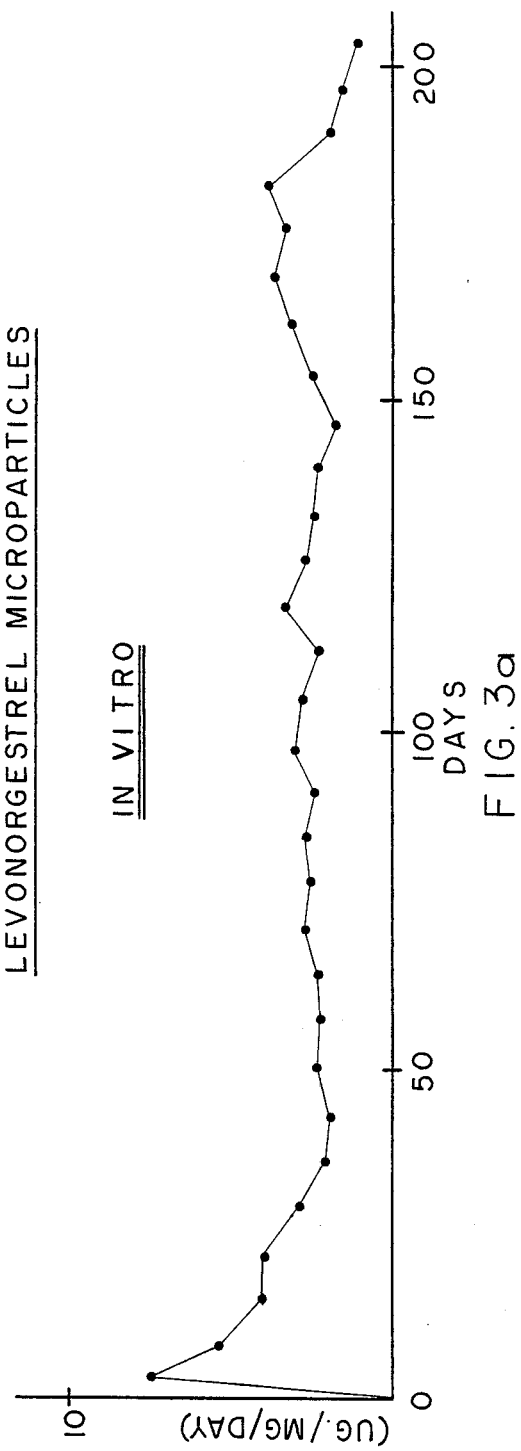
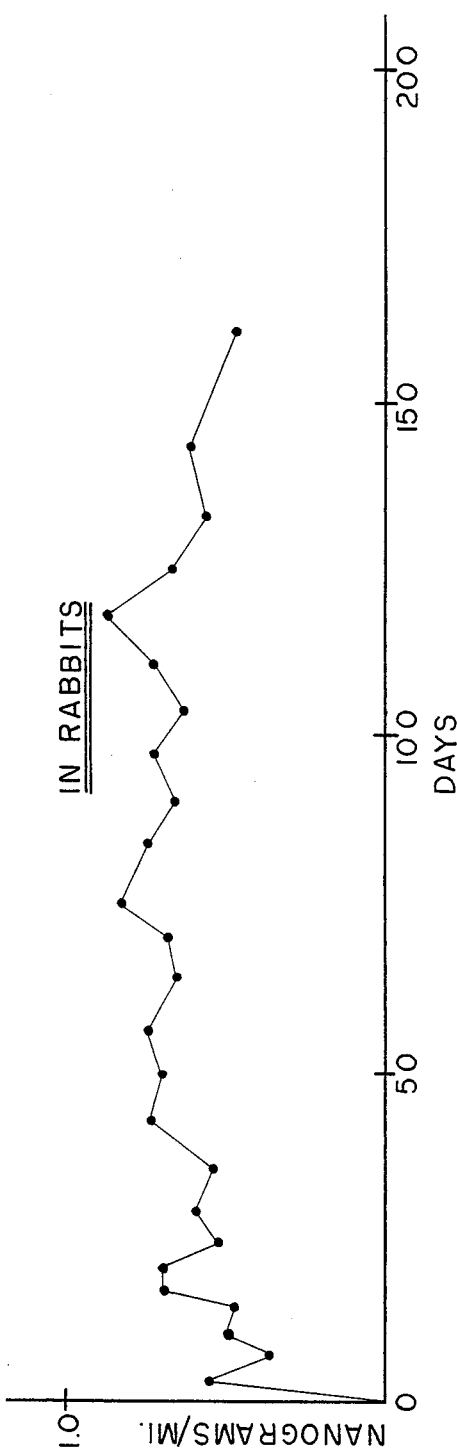

METHOD OF TRANSDERMAL DRUG DELIVERY

This is a continuation of co-pending application Ser. No. 920,300, now abandoned, filed on Oct. 17, 1986, which is a continuation-in-part of U.S. Ser. No. 653,362, filed Oct. 1, 1984 and now U.S. Pat. No. 4,624,665 which application is incorporated by reference in its entirety.

REFERENCE TO PRIOR APPLICATIONS

This application discloses to a prior co-pending application, U.S. Ser. No. 577,079, filed Feb. 6, 1984, entitled COMPOSITE CORE COATED MICROPARTICLES AND PROCESS OF PREPARING SAME, now U.S. Pat. No. 4,568,559 issued Feb. 4, 1986. The prior application relates to a process for preparing coated solid microparticles and to the microparticles so prepared and to the use of the microparticles to provide for the sustained release of a drug incorporated in the microparticles. The process comprises preparing a solvent solution of an active ingredient, such as a drug to be encapsulated, but more particularly a contraceptive steroid-type drug and a film-forming polymer and removing the solvent to provide a dry, composite, uniform admixture of the drug-active ingredient and the polymer material. The mixture is then reduced to a defined, smaller particle size distribution and the ground admixture then coated in a fluidized bed with a uniform, defined wall thickness of the same or substantially the same film-forming polymer material used to provide the composite core coated microparticles. Typically, the dry–composite admixture is reduced to a particle size of less than 1000 microns, e.g. 200 microns. The film-forming polymer material employed generally is a polymer, like polyvinyl alcohol or a cellulosic material or a biodegradable polymer, such as for example, a polylactide, a polyglycolide and copolymers of lactides and glycolides. The drug employed in the microparticles may vary, but typically may comprise, for example, a contraceptive seroid-type drug such as levonorgestrel or estrodiol. For injectable compositions, the particle size of the microparticles is less than 200 microns with a uniform wall coating of about 0.2 to 20 microns. The microparticles are useful for the controlled release of a drug-active ingredient such as in a zero order release pattern and, for example, may be employed by injecting microparticles suspended in a liquid carrier into a patient.

BACKGROUND OF THE INVENTION

Transdermal delivery of medication is not a new concept, as a variety of medications that are readily available for delivery through the skin have been available in ointment form for over thirty years. With ointments, however, it is difficult to achieve precise drug dosage. In a transdermal patch system, this problem is eliminated by controlling the rate of drug release over a prescribed period of time. Patches are worn behind the ear, on the chest, or on the arm and dispense a drug for as long as a week at a time. For certain drugs, transdermal delivery has significant advantages over oral administration. It eliminates "first pass" inactivation by the liver and irregular gastric absorption. Because of constant absorption through the skin, it maintains relatively constant blood levels of the drug.

Two drugs, scopolamine and nitroglycerin, have recently become commercially available in transdermal form. Although there are differences in composition and the mechanism of drug delivery among the available transdermal delivery systems, they all appear to be functionally similar. Generally, the systems have essentially steady state reservoirs sandwiched between an impervious backing and a membrane face. The systems usually are attached to the skin by an adhesive gel. Some products have a rate-controlling outer microporous membrane. One product depends on a diffusion matrix in which nitroglycerin molecules are in equilibrium between lactose crystals and the liquid phase. In another product, micropockets of nitroglycerin are evenly dispersed throughout a silicone polymer which controls the drug release rate and prevents dose dumping.

A description of the different commercial products which deliver nitroglycerin transdermally is set forth by Dasta et al, *American Pharmacy*, NS22, 2, 29–35, February, 1982, which article also illustrates the various prior art nitroglycerin patches and their construction and operation, and which article is hereby incorporated by reference.

U.S. Pat. No. 4,336,243, issued June 22, 1982, describes transdermal nitroglycerin pads wherein the pad comprises a silicone polymer matrix being a cross-linked silicone rubber having from about 10 to 200 microns microseal compartments formed by the in situa cross-linking of the silicone rubber after it is admixed with a hydrophilic solvent containing the nitroglycerin in a hydrophobic solvent which enhances the dispersion and transport. U.S. Pat. No. 4,053,580, issued Oct. 11, 1977, describes an earlier pharmaceutical delivery device employing a silicone polymer matrix wherein the rate of release of the active ingredient is controlled by altering the solubility of the hydrophilic solvent system for the polymer matrix.

Another polymer diffusion matrix transdermal delivery system is described is published European application No. 80300038.9, of A. Keith, entitled "Polymeric Diffusion Matrix and Method of Preparation and Drug Delivery Device Comprising Said Matrix". This application describes a polymeric diffusion matrix composed of glycerol and polyvinyl alcohol together with a water-soluble polymer to provide a polymer matrix capable of sustained release of a drug dispersed in the matrix. Typically, the water soluble polymer comprises a polyvinylpyrrolidone or a water soluble cellulosic derivative. U.S. Pat. No. 3,797,494, issued Mar. 19, 1974, describes a transdermal bandage which includes a reservoir with a drug confined within the interior chamber of the reservoir and distributed throughout a reservoir matrix. In one embodiment, the drug is released by a controlling microporous material, which microporous material meters the flow of the drug into the skin at a controlled rate. In another embodiment, an adhesive coating is uniformly distributed through microcapsules comprising a drug encapsulated with a microporous rate controlling material.

While many transdermal drug delivery systems have been described as economical and effective, a transdermal drug delivery system, particularly for the delivery of contraceptive steroid drugs, is still needed, and desired, particularly percutaneous delivery of steroid contraceptives in a controlled manner for periods of time ranging from one to four weeks or more.

Levonorgestrel is a synthetic steroid which has powerful progestational activity with minimal side effects at very low doses. Estradiol is a natural estrogen which has limited oral effectiveness because of "first pass" inactivation during circulation. On the other hand, the synthetic steroid, ethinylestradiol, is active orally, since its inactivation by the liver and other tissues is very low. These contraceptives and others like Mestranol, Morethindrone, etc., are employed in various oral contraceptives manufactured in this country. Although levonorgestrel pills contain 150 micrograms of the drug, studies with implantable drug delivery systems indicate that only 30 micrograms per day are sufficient to prevent fertility.

Thus, it is desirable to provide an effective transdermal drug delivery system for the transdermal delivery of drugs, particularly contraceptive steroids.

SUMMARY OF THE INVENTION

The invention concerns a transdermal drug delivery system and a method of manufacture and use of such system. In particular, the invention relates to a transdermal drug delivery system particularly useful for the controlled release of a contraceptive steroid drug or a combination of such drugs.

The invention relates to a transdermal drug delivery system which may be employed with a drug which is desired to be delivered transdermally at a controlled or sustained rate, typically a zero order rate or other delivery release patterns as desired. The transdermal drug delivery system of the invention prevents dose dumping of the drug caused by accidental rupture of the retaining member and ensures effective and prolonged delivery of the drug.

The invention relates to a method of and system for accelerating the transdermal delivery of drugs into a patient by sealing the skin of the patient with a thin, liquid film layer of a base material to occlude the skin and transporting a desired dosage of the drug across the thin layer typically from a rate-controlling system in contact with the thin layer. The rate-controlling system may be a thin rate-controlling membrane interposed between the drug and the thin layer. Preferably, the rate-controlling system comprises microparticles of the drug or a combination of drugs to be delivered suspended in the same or similar viscous base material and contained within a container system. The container system may comprise a macroporous, non-rate-controlling face membrane with an impervious backing to form a pool or patch-like system of desired face membrane area with the face of the membrane placed over and in contact with the thin, occluding, viscous layer on the skin. The thin viscous layer may be coated or placed on the skin repeatedly, and the patch system placed on top of the thin, viscous layer or the viscous layer formed in situ by exudation through the membrane face when the patch or pool system is placed in position on the skin. The patch or pool container system generally is retained in a transdermal position by the use of a peripheral adhesive layer about the patch or pool. Typically, the face or transport area of the membrane is covered prior to use by a removable cover such as a peelable strip of impervious sheet material.

In another embodiment, microcapsules containing a drug for delivery may be suspended in a viscous base material, and the composition then spread as a layer over the skin of the user with or without a covering material.

The present drug delivery system for the transdermal delivery of medicaments is based on the use of solid microparticles. The system releases the drug from rate-controlling microparticles which are suspended in a dermatologically acceptable viscous liquid base. Drug release from microcapsules is controlled by microcapsule size and wall thickness. The system is also characterized by the selection of the base material which delivers a thin, liquid, melted film of the base vehicle to the skin and whose function is to deliver the drug to the skin. The function of the viscous liquid film is to occlude the skin causing the stratum corneum to swell and hydrate by forcing the diffusion of water from the lower layers of the epidermis and thus to accelerate the drug delivery. The first phase in transdermal delivery is dependent on the rate of diffusion of the drug within the vehicle and its rate of release from the vehicle. The drug concentration in the vehicle determines the thermodynamic activity and influences the diffusion of the drug out of the vehicle.

The present drug delivery system suspends drug/polymer microparticles in a delivery vehicle composition which microparticles control the rate of release of the drug to the vehicle. Drug delivery from microcapsules in zero-order provided solid particles are present inside the microcapsule in equilibrium with a saturated solution of the drug. It is dependent on the diffusion coefficient of the drug in the polymer, the thickness of the capsule wall and the microcapsule dimensions in accordance with this equation:

$$\frac{dM_t}{dt} = 4\pi DK\Delta \frac{r_o r_i}{r_o r_i}$$

where M is the mass of the drug released, dM/dt is the steady state release rate at time t, DK is the membrane permeability, D is the diffusion coefficient of the drug in the membrane in cm$^2$/sec., K is the distribution coefficient, C is the difference in drug concentration between the internal and external surface of the membrane, and $r_o r_i$ are the outer and inner radii of the capsule wall, respectively.

Drug release from monolithic microparticles such as microspheres is first order and is additionally dependent on drug concentration in the particle. Thus, the presence of the microparticles in the base vehicle helps to maintain a constant thermodynamic activity of the drug in the vehicle by insuring that the concentration of the drug is close to saturation.

The principal barrier to permeation of small molecules through the skin is provided by the stratum corneum or "horny layer" of cells which is about 10 to 15 microns thick. This layer is composed of a dispersion of hydrophilic proteins in a continuous lipid matrix. The lipid component of the layer which comprise only 20% to 30% of the weight of the tissue are directly responsible for its unique low permeability (Scheuplein, 1971). The stratum corneum may be regarded as a passive diffusion membrane, albeit not entirely inert, which follows Fick's Law in which the steady state flux Js is:

$$J_s = \frac{K_m D C_s}{S}$$

where $K_m = \frac{\text{solute sorbed per cc of tissue}}{\text{solute in solution per cc solvent}} = \frac{C_m}{C_s}$ Cs = concentration difference of solute across membrane.

D = average membrane diffusion coefficient for solute.
S—membrane thickness.

Swelling of the corneum can be produced by hygroscopic or other substances if they penetrate the hydrophilic zone or if lipophilic substances penetrate the hydrophobic zones. Increasing the state of hydration increases the porosity and thickness of the layer and favorably influences the transport of the drug by two to threefold. The simplest method for increasing hydration is to occlude the skin which forces the diffusion of water from the lower layers of the epidermis. Estimated diffusion constant for low molecular weight non-electrolyte is ESN $10^{-9}$ cm. sq./sec. for stratum corneum and ESN $10^{-6}$ cm. sq./sec. for the dermis.

The degree of hydration of the stratum corneum is provided by the base material which provides a thin, liquid film to its outer surface to occlude the skin. The liquid film is simultaneously in contact with the skin and the semi-solid viscous or solid base material of the reservoir.

Following topical administration of many drugs, including steroids like estrogen and norgesterone, a reservoir can form in the skin. The existence of this reservoir and its localization in the stratum corneum was first proven by Vickers (1963). Much of the work in this area has dealt with local action of drugs (e.g. hexachlorophene, sunscreens, cortisol). However, prolonged toxic response following topical administration of vasoconstrictors demonstrates that a cutaneous reservoir can provide sustained release into the systemic circulation. Accumulation of both estrogen and progesterone is subcutaneous tissue and underlying muscle has been observed and is more pronounced with percutaneous than with subcutaneous administration. The duration of the local reservoir appears to be dependent on the normal 14-day cycle of epidermal turnover. Irritation with a detergent of methotrexate increases turnover and can reduce the duration of the reservoir by nearly 50%. Inhibition of turnover with fluorinated steroids can double the duration to 28 days. In addition, a compound which very rapidly penetrates and diffuses is maintained in the reservoir for a short period of time (e.g. nicotine, 3 to 4 days). Since occlusion of the area of application appears necessary to promote sustained absorption from the reservoir, continued absorption following removal of the delivery system should be minimal unless the concentration is very high.

Pronounced and prolonged effects of estrogens and gestagens can be expected by the transdermal route since it is the total amount of hormone absorbed by the body that is decisive, and not the peak height of the hormone level. The flux rate of steroids through human skin has been studied by others and are shown below in Table 1.

TABLE 1

| | Flux Rates of Steroids | |
|---|---|---|
| | FLUX (MOLES/CM$^2$ HR.) | |
| (Steroid 1979) | (Feldman 1969) | (Schaefer) |
| 17$^B$ estradiol | 8.2 × 10$^{-11}$ | 5.8 × 10$^{-10}$ |
| 17$^B$ estradiol | | 4.6 × 10$^{-10}$ |
| Testosterone | 5 × 10$^{-11}$ | 1 × 10$^{-9}$ |
| Estriol | | 7.8 × 10$^{-11}$ |
| Progesterone | 3.4 × 10$^{-11}$ | |
| Hydrocortisone | 2.5 × 10$^{-11}$ | |
| Corticosterone | 7.5 × 10$^{-12}$ | |

Table 1 shows that the flux rates of estradiol and progesterone are fairly high in comparison to the corticosterones. These flux rates depend on the concentration of the applied substance in the vehicle. At low concentrations, the rates are proportional to the concentrations in the vehicle. This proportionality is not 1 to 1 since a doubling of the concentration increases the flux by about 30% to 50%.

This general pattern of regional variation was found to hold for other chemical moieties (steroids, pesticides and antimicrobials). Although the stratum corneum is generally accepted to be the major barrier to percutaneous penetration, this appears to hold only if the skin is intact. Damage to the stratum corneum makes the other layers function as barriers. For example, the penetration of hydrocortisone through modified skin results in a tenfold increase in the penetration of hydrocortisone from 1% to 10% when the skin is occluded. The thin, liquid film which is exuded by the macroporous membrane occludes the skin to increase drug penetration.

The drug delivery system is based upon the use of drug-polymer solid microparticles or rate-controlling microcapsules which are dispersed and suspended in a dermatologically-acceptable viscous liquid base material or vehicle, which base material is a solid or semi-solid material selected to to melt or liquefy at or about the skin or body temperature of the user. Typically, the body temperature is about 37° C. while the skin temperature is slightly lower, i.e. 34° C. to 35° C. The outer rim or perimeter of the reservoir or container of the base material is covered by a non-sensitizing, hypoallergenic adhesive layer or other means to secure the system to the skin which holds the solid base material in contact or adjacent to the skin and prevents loss of the drug to the surrounding area. The microcapsules release the drug into the base in a controlled release pattern and maintains it in a thermodynamically stable condition. Release is controlled by the selected microcapsule size and thickness of the microcapsule wall. Intimate contact between the skin and the thermodynamically stable, viscous, thin film base also ensures uniform delivery of the drug throughout the treatment period.

Microparticles are suspended in the base material to provide a thermodynamically stable base with a constant driving force of the drug in the base material. The microparticles or microspheres suspended in the base material comprise solid mixtures of the drug in a polymer, and one embodiment may comprise the microparticles as described in the assignee's co-pending application Ser. No. 577,079, now U.S. Pat. No. 4,568,559.

The reservoir comprises a dermatologically-acceptable, generally viscous, semi-solid or solid base material. The viscosity should be sufficient to suspend the microparticles therein and to prevent leakage or excessive flow. A plurality of solid microparticles or microspheres are generally uniformly dispersed and suspended in the base material within the reservoir. The microparticles include an effective therapeutic amount of an active drug ingredient or combination thereof, such as a contraceptive steroid, like levonorgestrel or estradiol or a combination thereof for transdermal delivery for a particular therapeutic purpose such as contraception. The drug is present in an effective therapeutic amount within the microparticles suspended in the base material with the microparticles generally designed to provide for a zero order release of the active drug material. Preferably, the microparticles are composed of an admixture of a polymer with the active drug ingredient in the microparticles varying as desired, but generally from about 0.1% to 30% by weight, for example, 1% to 20%, and wherein the microparticle has a thin polymer wall coating thereon, such as a wall coating imparted in a fluid bed coating system or by other means. Typically, an adhesive layer is placed about the periphery of the drug delivery system and usually an impermeable material such as a protective peel strip is secured to the open face of the reservoir, which peel strip is to be removed just prior to use.

In use and on removing of the peel strip, the drug delivery system in the form of a patch is applied to the skin of the user at a desirable location and the patch adhered by an adhesive exposed after removal of the peel strip. On placing the solid base material in contact with the skin of the user, the base material liquefies or melts to form a thin, liquid layer on the user's skin, thus forming a thin, thermodynamically stable thin film. The active drug ingredient is released at a selected zero order rate from the plurality of microparticles suspended in the base material; and therefore, transported directly through the solid base material and the thin, liquid film into the skin of the user. The drug delivery system of the invention contributes significantly to the accelerated permeation of the drug through the skin, since the skin is continuously in contact with the drug in solution. Further, since the skin is occluded to permit hydration of water from the lower layers, the permeation of the drug from the base material into the hydrated stratum corneum is much faster than when a dry, dehydrated corneum is presented. In addition, the skin is continuously in contact with the melted liquid film of the base material which is generally selected to have emollient properties. This emollient contributes to the accelerated delivery by maintaining the outer skin softness and pliability to assure continuous contact between the skin, the base material and the membrane surface which is in quite a contrast to contact with a dry, solid matrix of the prior art.

The drug-polymer microparticles produce a thermodynamically stable liquid base as a source of the active drug and practically eliminates the problem of drug dose dumping if the membrane is accidentally ruptured as with prior art transdermal drug delivery systems. The rate of drug delivery may be modified and tailored by several variables, such as the microparticle size, composition, polymer composition, wall thickness and the selection of the base composition and properties as to the degree of hydrophilicity or hydrophobicity. Various additives may be compounded and added into the base material, which compounds may be employed to impart special properties to the base material; for example, to enhance diffusion, control steroid reservoir formation, improve antiseptic properties, reduce infection, control viscosity or to add emollient or lubricant properties where prolonged usage of the transdermal drug delivery system is desired.

The base material may comprise a variety of materials, but typically should be a solid-type material capable of suspending the plurality of solid microparticles therein and also to liquefy or melt on contact with the user's skin, i.e. to have a melting temperature of about 33° C. to 38° C., so as to form a thin, thermodynamically stable, liquid film on the skin of the user. The viscosity of the base material should be high enough so that the liquid base material will not run and deplete the reservoir or become messy to the user. Typically, the base material should have a semi-solid or solid gel or grease-like viscosity and properties.

The base material should be selected to be compatible with and to permit the transport of the drug within the microparticles. Typically, if the drug is a low water soluble-type drug, then the base material would be a low water soluble base material generally matching the hydrophobicity of the drug, and vice versa, where the drug is water soluble, the base material may be selected to be also water soluble so that there is transport and compatibility from the drug release through the wall of the microparticle and so the drug may move effectively through the base material and onto the thin film adjacent the user directly into the skin of the user. For example, the liquid base material may comprise a hydrophobic material, such as a long chain, e.g. $C_8$ to $C_{22}$, hydrocarbon-type material, particularly for use with water insoluble or very low water soluble drugs, such as for example, a grease-like hydrocarbon such as a petroleum-based jelly, e.g. vaseline, a semi-solid mixture of hydrocarbons having a mp of 38° C. to 60° C. The base material may comprise also a hydrophilic-type material such as a polyalkylene polyol, such as a polypropylene glycol and polyethylene glycol or glycerol, or a water solution placed in a gel-like form through the use of viscosity-modifying additives or gel-like material, such as polyvinylpyrrolidone, agar, proteins, thickeness and the like. The polyethylene glycols generally have molecular weights of about 800 to 3000. The polyalkylene glycols are employed generally in combination with water, e.g. up to 20% by weight, to form a soft, meltable composition. In addition, it should be noted that the base material in the reservoir may contain other modifying additives to impart other desirable properties, such as the use of emollients such as glycols like glycerine, viscosity controlling agents, preservatives, thickening agents, antibacterial agents, such as quaternary ammonium compound, stabilizers, depletion-indicating devices such as dyes, waxes and other material typically employed in pharmaceutical and cosmetic applications and which are dermatologically and pharmaceutically acceptable.

The microparticles employed in the drug delivery system generally comprise solid microparticles wherein the core of the particle contains an admixture of a polymer together with one or more of the drugs which are to be delivered by the microparticles, the active ingredient in the core may comprise a varying amount and range, for example, from 5% to 95% by weight, such as 20% to 80% by weight, with the remainder made up of a core polymer material. The amount of microparticles in the base material may vary and range from 5% to 70%, e.g. 10% to 30%, by volume of the reservoir material. The microparticle comprises and has a wall thickness of generally the same or similar polymer as the core material. The core material, of course, may have other additives, such as binders, adhesives, fillers and the like. The microparticles may have a wall coating produced by coating of the solution in the fluidized bed to provide a generally uniform wall thickness.

The active drug ingredient may comprise a wide variety of materials or combinations and be selected for the particular therapeutic function desired to be transdermally released. Preferably, the active drug ingredient does not react with and is chemically inert with the base material and with the synthetic film forming polymer material comprising the microparticle. The microparticle is generally less than 1000 microns and typically less than about 200 microns. The microparticles may comprise microspheres and the microparticles designed to deliver a constant and sustained dose of the active ingredient for periods ranging from several hours to several years, for example, one day to one month. In one embodiment, the control release rate may be a zero order release rate. The microparticles may be formed of natural or synthetic polymer materials both of the core material and the coating material and particularly with biodegradable polymers such as the lactides, glycolides, or copolymers of lactide and glycolide as biodegradable polymers. For example, in one embodiment, microparticles may be prepared from employing an active drug steroid, such as levonorgestrel and estradiol, and combinations in admixture with a biodegradable (polylactide) polymer and then coated with a biodegradable (polylactide) polymer to prepare the microparticles.

The drug material to be used as the active ingredient may very and comprise for example, antibiotics, antibacterial agents, hormones, steroids, or other therapeutic agents. However, the principles of the drug delivery system will be illustrated employing a contraceptive steroid hormone with a drug delivery system designed to provide for sustained release by transdermal delivery of a contraceptive hormone, such as levonorgestrel or estradiol. The sustained release of the drug from the microcapsules should be such as for an effective amount to be transdermally delivered to the user in an amount to be effective for the purpose for which the drug is selected. For example, with contraceptive steroid hormones, approximately 5 to 150 micrograms per day per use and generally 20 to 50 micrograms per day is sufficient to prevent female fertility when using a levonorgestrel drug as an active ingredient.

The drug delivery system may be in the form of a patch or bandage having a reservoir containing the base material which is placed in contact with the skin through the thin, thermodynamically liquid, melted layer. Typically, the area of the liquid film would range from about 1 to 30 square centimeters, and more typically, 2 to 10 square centimeters.

The invention will be described for the purposes of illustration only in connection with cetain embodiments; however, it is recognized that various changes, modifications, additions and improvements may be made to the illustrated embodiments by a person skilled in the art all falling within the spirit and scope of the invention.

BRIEF DESCRIPTION OF THE DRAWINGS

FIG. 3 (a and b) is a graphical representation of the comparison of in vitro release and plasma levels of levonorgestrel from mirocapsules.

DESCRIPTION OF THE EMBODIMENTS

Figure 1:
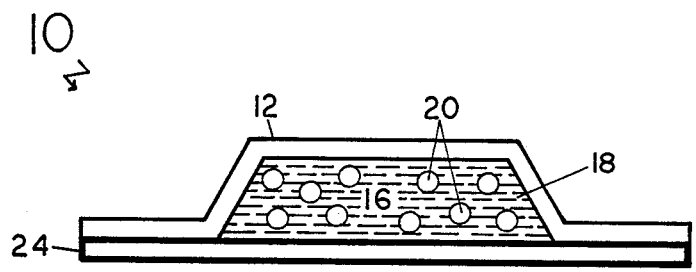
FIG. 1 is a schematic, sectional, illustrative view of the drug delivery patch system of the invention.
Figure 2:
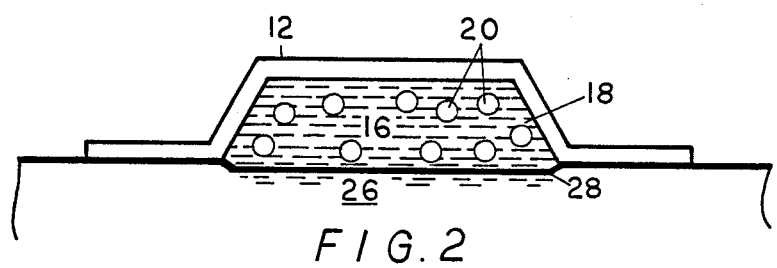
FIG. 2 is a schematic, sectional and illustrative view of the patch delivery system of FIG. 1 as applied to the skin of a user.

FIGS. 1 and 2 show a bandage-type, transdermal, sustained-release delivery system of the invention 10 wherein the device comprises an impervious backing sheet 12 defining a reservoir. The U-shaped backing sheet 12 forms a generally flat reservoir, the resevoir containing a base material 18 composed of 86% by weight of polyethylene glycol 1450 and 14% water. The base material composition had a consistency of a soft solid at room temperature, but becomes fully liquid at temperatures at or above 30° C. The base material becomes fully liquid at lower temperatures if the water content is increased, e.g. at 20% water, the melting point is 24° C. so that a macroporous face membrane as in the parent application may be necessary. On contact with the skin of a user, the soft solid base material becomes liquid and forms a thin liquid film on the user's skin. Uniformly suspended in the soft base material are a plurality of solid microparticles 20 containing, for example, levonorgestrel in an amount to deliver about 30 micrograms per day of the levonorgestrel from the microparticles in a zero order release over a period of one to four weeks. The microparticles 20, for example, as prepared in the co-pending application, generally comprise from about 5% to 75% by weight of the viscous base material within the reservoir 16, e.g. 20% to 60%. Around the peripheral edge of the backing material is an adhesive layer 22 while a removable peel strip 24 prevents the discharge of the base material from the reservoir prior to use. A peel strip is not required since the solid base material will remain in the reservoir, but is practical to protect the base material until use.

FIG. 2 shows the application of the bandage-type delivery system to the skin of a user 26 and shows a thin, melted liquid film 28 of the base material 18 in the reservoir forms to maintain intimate contact between the skin 26 and the solid base material 18 to accelerate the transdermal delivery of the drug from the microcapsules 20.

A typical sustained release for the release of levonorgestrel is: a 9.4 square centimeter of Johnson and Johnson Rayon ™ First Aid Tape-Hypo-Allergenic =1 inch wide, 1.5 inches long, for the impervious backing and to form the adhesive layer, and a 2 square centimeter ID—2.25 square centimeter OD—⅜mm thick Teflon ring. Microparticles are prepared from the levonorgestrel and the poly-L-(—)lactide as follows: Prepare a 2.5% wt/v solution of polyvinyl alcohol (PVA) #523 in one liter of distilled water; prepare at 15% wt/v solution of poly-L-(—)lactide, approximately 1 R.S.V. in 300ml of reagent grade methylene chloride; mix 5ml of the poly-L-(—)lactide solution, 10ml methylene chloride and 5 grams of levonorgestrel to form a uniform slurry; take the 1 l of PVA solution and pour it into a 2 l stainless steel beaker. Stir at approximately 1000RPM (1550 ×0.7) and heat at a low temperature (approximately 35° C.); add levonorgestral slurry. Heat approximately four hours, then turn off heat and stirrer; wet sieve off the 45–106 um size fraction; and dry in vacuum oven at room temperature and recover the solid micropshres. Then 45mg of these solid microspheres are mixed with the soft base vehicle. The Teflon ring is placed in the center on the adhesive side of the tape, and the base material is then spread to uniform thicknss inside the Teflon ring and the strip 24 used to seal the reservoir. An estradiol patch may be similarly prepared with 38mg of microspheres containing estradiol.

FIG. 3(a) illustrates an in vitro sustained release of levonorgestrel from a microparticle wherein the drug comprises about 10% of the microparticles and the biodegradable polymer of polylactide comprises about 90% by weight of the core material and wherein the wall thickness of the microparticles ranges from about 3 to 8 microns and is composed of the polylactide polymer.

FIG. 3(b) illustrates the in vivo release of the hormone levonorgestrel into blood plasma of rabbits from the sme microparticles as in FIG. 3(a). Thus, it is illustrated that the levonorgestrel microcapsules provide for a sustained, generally zero order release of the contraceptive.

A transdermal delivery system known as DermaPatch TM has been developed which delivers levonorgestrel across freshly excised mouse skin at a dose of 43 micrograms/day from a 2.4 square centimeter patch. Drug release is sustained at a constant rate over a minimum period of 14 days. A system which delivers estradiol across freshly excised mouse skin at a dose of 5 micrograms/day from a 2.4 square centimeter patch has also been developed. A combined contraceptive system would constitute 20 micrograms/day of levonorgestrel, and 25 micrograms/day of estradiol over a period of 3 to 7 days, which target doses can be delivered from a single 5 to 6 square centimeter patch system which contains both steroids.

In vitro mouse skin permeation studies were conducted with a 2.4 square centimeter patch which was placed in a 20mm diameter water-jacketted Franz diffusion cell mounted on a 9-cell Drive Unit/Mounting Assembly. The water jacket temperature of the cells was controlled by a bath and water circulator which is maintained at 37° C. This system is widely used in the pharmaceutical industry for measuring the permeability of percutaneous patches across animal and cadaver skins. In the preliminary studies with levonorgestrel and estradiol, it was discovered that the size of the cell reservoir was too small to permit overnight studies within a few hours after startup so an adapter was used for the Universal Diffusion Cell to permit overnight studies.

Release of each drug was determined as a function of time by analysis of aliquots of the contents of the reservoir in a Waters High Pressure Liquid Chromatograph (HPLC) using a u Bondpak C-18 radial pack column with a mobile phase of 60% ethanol in water. The steroids were measured in a uv detector at a wavelength of 280 nm for estradiol and 254 nm for levonorgestrel.

Pieces of full thickness abdominal skin were freshly excised from six-week-old male nude mice and mounted individually on the Franz diffusion cell. Before use, the skins were washed three times in 200ml normal saline to remove extraneous and other soluble material. The face membrane of the system was applied to the stratum corneum side of the skin. The skin permeation profile of each drug was followed by removing the liquid from the receptor compartment for assay at the appropriate intervals. The compartment was then filled with fresh saline and the permeation continued. Release of the drug was monitored in a liquid chromatograph (HPLC).

The results of the skin permeation studies indicated that levonorgestrel penetrates the abdominal skin of the nude mouse at a zero order rate. The rate of the skin permeation for levonorgestrel delivered by the system during 24 hours is approximately 43 ug/day. The area of the membrane in contact with the skin was 2.4 square centimeters. This translates into a skin permeation rate of 1.8 ug/square centimeter/hour or 18 ug/square centimeter/day. This rate continued for a period of 14 days.

Table 2 summarizes the test data on levonorgestrel and estradiol mouse skin permeation tests:

TABLE 2

| Levonorgestrel Micrograms/ 2.4 sq. cm. | Days | Estradiol Micrograms 2.4 sq. cm. | Days |
| --- | --- | --- | --- |
| about 25 | 1 | 6 | 1 |
| 90 | 2 | 10 | 2 |
| 140 | 3 | 16 | 3 |
| 270 | 7 | | |
| 375 | 8 | | |
| 405 | 9 | | |
| 570 | 10 | | |
| 505 | 11 | | |
| 590 | 14 | | |

To obtain maximum flux rates, aliquots of the reservoir were analyzed during a period of 8 hours on day 2, day 3, and day 7. The results show zero order release of the hormone from the system on each of the three days at an average rate of 6.7 micrograms per hour (160 micrograms per day/2.4 square centimeters). Thus, a patch with a reservoir surface area of 0.5 square centimeters should be capable of delivering 20 micrograms per day of levonorgestrel.

Tests were also conducted with an estradiol-containing patch system with the 2.4 square centimeter estradiol patch, and permeation rates of 5 per days were achieved. At this rate, a patch with a surface area of 5 square centimeters would be capable of delivering 2.5 milligrams per day of levonorgestrel.

Table 3 sets forth the properties of a patch-type sustained release system;

TABLE 3

Properties of DermaPatch TM Sustained Release System

| | Levonorgestrel | Estradiol |
| --- | --- | --- |
| System Characteristics | | |
| Surface area, sq. cm. | 2.4 | 2.4 |
| Loading dose, mg. | 31 | 32.6 |
| Mouse Skin Permeation | | |
| Rate of permeation mcg./sq. cm./hr. | 0.75–2.8 | >0.09* |
| Minimum dose absorbed, mcg./24 hr. | 43–160 | >5.2* |
| Period permeation studied, days | 14 | 3 |
| Estimated Patch Size Required | | |
| Dose required, mcg./day | 20 | 25 |
| Estimated size needed to deliver required dose, sq. cm. | 0.5 | 5 |
| Expected duration, days | >7 | >7 |

*These are minimum values which have not been corrected for saturation effects. It is expected that the maximum flux rates will be nearly 2 to 3 times greater.

LIST OF REFERENCES

Dasta, J.F. and Geraets, D.R., Topical Nitroglycerin: A New Twist to an Old Standby, *Am. Pharm.* NS22 (2), 29 (1982).

Feldman, R.J. and Maibach, H.I., *J. Invest. Derm.* 52, 89 (1969).

Shaefer, H., Stuttgen, G. and Schalla, W., Contraception via Topical Application?—A Review, *Contraception*, 20 (3), 225 (1979).

Scheuplein, R.J. and Blank, I.H., Permeability of the Skin, *Physiol. Rev.* 51, 702 (1971).

Vickers, C.F. H., *Arch. Dermatol.* 88, 20–25 (1963).

What is claimed is:

1. A transdermal drug delivery system, which system comprises:
(a) an impervious backing sheet;

(b) the reservoir containing a transdermal drug delivery composition, which comprises:
  (i) a dermatologically-acceptable, semi-solid or solid base material, which base material is selected on application to the skin of the user to melt or liquefy and form a thin, liquid film and to occlude the skin of the user and to force hydration of the stratum corneum layer with water from the lower layers of the epidermis of the user in use;
  (ii) a plurality of solid polymeric microparticles generally uniformly dispersed and suspended in the base material in the reservoir, the microparticles having a particle size of less than about 1000 microns and containing an effective, therapeutic amount of a drug for transdermal delivery in a controlled release pattern, the active drug material for transdermal delivery and the base material being compatible to form a compatible transport relationship; and
  whereby, on application to the skin of a user the base material melts or liquefies to form a thin, liquid film on the skin of the user, while the drug is released at a controlled release rate from the suspended microparticles into the solid or semi-solid base material and through the liquid film directly into the skin of the user.

2. The drug delivery system of claim 1 wherein the base material melts and forms a liquid at about 34° C. to 37° C.

3. The drug delivery system of claim 1 wherein the base material comprises a hydrophilic material and the drug to be delivered comprises a water soluble drug.

4. The drug delivery system of claim 1 wherein the base material comprises a hydrophobic material and the drug to be transdermally delivered comprises a hydrophobic drug.

5. The drug delivery system of claim 1 wherein the base material comprises a glycerol, water-containing, liquid-base material and wherein the drug to be transdermally delivered comprises a water soluble drug.

6. The drug delivery system of claim 1 wherein the base material comprises a hydrocarbon material and wherein the drug to be transdermally delivered comprises a hydrophobic drug soluble in the hydrocarbon base material.

7. The drug delivery system of claim 1 wherein the active drug comprises a steroid hormone.

8. The drug delivery system of claim 7 wherein the steroid hormone comprises norethindrone, norgestrel, estradiol, levonorgestrel and mestranol and combinations thereof.

9. The drug delivery system of claim 1 wherein the base material comprises a mixture of a polyalkylene glycol and water.

10. The drug delivery system of claim 1 wherein the base material comprises a mixture of polyethylene glycol and up to 20% by weight water.

11. The drug delivery system of claim 1 which includes a means to seal the face of the reservoir prior to use; and means to secure the membrane face to the skin of the user.

12. The drug delivery system of claim 1 wherein the microparticle comprises a microparticle having a particle size of about 200 microns or less and wherein the active ingredient comprises a levonorgestrel or estradiol wherein the active drug is admixed with a lactide or glycolide polymer and wherein the microparticle has a wall composed of a lactide or glycolide polymer.

13. The drug delivery system of claim 1 wherein the microparticles comprise a solid admixture of the drug and a biodegradable polymer and a thin outer layer of a biodegradable polymer.

14. A composition for the accelerated transdermal controlled delivery of a drug to a user, which composition comprises:
  (a) a meltable semi-solid or solid base material, which, on application to the skin of the user, melts to form a thin liquid film and selected to occlude the skin of the user and to force hydration of the stratum corneum layer with water from the lower layers of the epidermis of the user in use; and
  (b) a plurality of solid polymeric microparticles generally uniformly dispersed and suspended in the base material, the microparticles having a particle size of less than about 1000 microns and containing an effective, therapeutic amount of a drug for transdermal delivery, the active drug material for transdermal delivery and the base material being compatible to form a compatible transport relationship;
  whereby, on application to the skin of a user of the transdermal drug composition the drug is released at a controlled rate from the suspended microparticles into the base material and into the skin of the user.

15. The composition of claim 14 wherein the base material melts and forms a liquid of about 34° C. to 37° C.

16. The composition of claim 14 wherein the base material comprises a glycerol, water-containing, liquid base material and wherein the drug to transdermally delivered comprises a water soluble drug.

17. The composition of claim 14 wherein the base material comprises a hydrocarbon material and wherein the drug to be transdermally delivered comprises a hydrophobic drug soluble in the hydrocarbon base material.

18. The composition of claim 14 wherein the active drug comprises a steroid hormone.

19. The composition of claim 18 wherein the steroid hormone comprises norethindrone, norgestrel, estradiol, levonorgestrel and mestranol and combinations thereof.

20. The composition of claim 14 wherein the base material comprises a mixture of a polyalkylene glycol and water.

21. The composition of claim 14 wherein the base material comprises a mixture of polyethylene glycol and up to 20% by weight water.

22. The composition of claim 14 wherein the microparticle comprises a microparticle having a particle size of about 200 microns or less, wherein the active ingredient comprises a levonorgestrel or estradiol wherein the active drug is admixed with a lactide or glycolide polymer and wherein the microparticle has a wall composed of a lactide or glycolide polymer.

23. The composition of claim 14 wherein the microparticles comprise a solid admixture of the drug and a biodegradable polymer and a thin outer layer of a biodegradable polymer.

* * * * *

UNITED STATES PATENT AND TRADEMARK OFFICE
CERTIFICATE OF CORRECTION

PATENT NO. : 4,834,978

DATED : May 30, 1989

INVENTOR(S) : Elie S. Nuwayser

It is certified that error appears in the above-identified patent and that said Letters Patent is hereby corrected as shown below:

Column 12, line 68, after "sheet" and before ";" insert --to define a reservoir--.

Signed and Sealed this

Sixth Day of February, 1990

Attest:

JEFFREY M. SAMUELS

Attesting Officer    Acting Commissioner of Patents and Trademarks